United States Patent [19]

Castro

[11] Patent Number: 5,389,081
[45] Date of Patent: Feb. 14, 1995

[54] STABILIZER FOR A VALVE ASSEMBLY FOR INTRODUCING INSTRUMENTS INTO BODY CAVITIES

[75] Inventor: Salvatore Castro, Seymour, Conn.

[73] Assignee: United States Surgical Corporation, Norwalk, Conn.

[21] Appl. No.: 63,255

[22] Filed: May 18, 1993

[51] Int. Cl.⁶ .............................. A61M 5/178
[52] U.S. Cl. ...................... 604/167; 604/256; 604/264
[58] Field of Search ............... 251/212, 298; 354/226, 354/270, 272, 274; 604/30, 158, 164, 167, 169, 249, 256

[56] References Cited

U.S. PATENT DOCUMENTS

| | | |
|---|---|---|
| 729,423 | 5/1903 | Scheiber et al. . |
| 2,797,837 | 7/1957 | Roberts . |
| 3,086,797 | 4/1963 | Webb . |
| 3,197,173 | 7/1965 | Taubenheim . |
| 3,438,607 | 4/1969 | Williams et al. . |
| 3,766,916 | 10/1973 | Moorehead et al. . |
| 3,788,318 | 1/1974 | Kim et al. ............... 604/164 |
| 3,811,440 | 5/1974 | Moorehead et al. . |
| 3,856,010 | 12/1974 | Moorehead et al. . |
| 3,875,938 | 4/1975 | Mellor . |
| 3,920,215 | 11/1975 | Knauf . |
| 3,970,089 | 7/1976 | Saice . |
| 3,977,400 | 8/1976 | Moorehead . |
| 3,994,287 | 11/1976 | Turp et al. . |
| 4,000,739 | 1/1977 | Stevens . |
| 4,149,535 | 4/1979 | Volder . |
| 4,177,814 | 12/1979 | Knepshield et al. . |
| 4,202,527 | 5/1980 | Price et al. ............... 251/212 |
| 4,231,400 | 11/1980 | Friedling et al. . |
| 4,240,411 | 12/1980 | Hosono . |
| 4,243,034 | 1/1981 | Brandt . |
| 4,324,239 | 4/1982 | Gordon et al. . |
| 4,378,013 | 3/1983 | LeFevre . |
| 4,424,833 | 1/1984 | Spector et al. . |
| 4,430,081 | 2/1984 | Timmermans . |
| 4,436,519 | 3/1984 | O'Neill . |
| 4,473,369 | 9/1984 | Lueders et al. . |
| 4,475,548 | 9/1984 | Muto . |
| 4,496,348 | 1/1985 | Genese et al. . |
| 4,580,573 | 4/1986 | Quinn . |
| 4,610,665 | 9/1986 | Matsumoto et al. . |
| 4,610,674 | 9/1986 | Suzuki et al. . |
| 4,626,245 | 12/1986 | Weinstein . |
| 4,634,421 | 1/1987 | Hegemann . |
| 4,654,030 | 3/1987 | Moll et al. . |
| 4,655,752 | 4/1987 | Honkanen et al. . |
| 4,673,393 | 6/1987 | Suzuki et al. . |
| 4,723,550 | 2/1988 | Bales et al. . |
| 4,786,028 | 11/1988 | Hammond . |
| 4,798,594 | 1/1989 | Hillstead . |
| 4,817,631 | 4/1989 | Schnepp-Pesch et al. . |
| 4,839,471 | 6/1989 | Clark et al. . |
| 4,842,591 | 6/1989 | Luther . |

(List continued on next page.)

FOREIGN PATENT DOCUMENTS

| | | |
|---|---|---|
| 0344907 | 12/1989 | European Pat. Off. . |
| 0350291 | 1/1990 | European Pat. Off. . |
| 2019219 | 10/1979 | United Kingdom . |
| 2065479 | 8/1981 | United Kingdom . |

*Primary Examiner*—C. Fred Rosenbaum
*Assistant Examiner*—Perry E. Van Over

[57] ABSTRACT

A stabilizer assembly for supporting a surgical instrument passed through an insufflation cannula assembly. The stabilizer assembly includes a housing having an aperture formed therein to allow passage of surgical instruments therethrough. Also provided on the stabilizer assembly are separate rigid instrument support members which are selectively operable to apply rigid support to surgical instruments passed through the stabilizer assembly.

14 Claims, 4 Drawing Sheets

U.S. PATENT DOCUMENTS

| | | | |
|---|---|---|---|
| 4,869,717 | 9/1989 | Adair . | |
| 4,874,377 | 10/1989 | Newgard et al. . | |
| 4,884,091 | 11/1989 | Nakagomi | 354/270 |
| 4,895,565 | 1/1990 | Hillstead . | |
| 4,909,798 | 3/1990 | Fleischhacker et al. . | |
| 4,917,668 | 4/1990 | Haindl . | |
| 4,929,235 | 5/1990 | Merry et al. . | |
| 4,943,280 | 7/1990 | Lander | 604/169 |
| 4,960,259 | 10/1990 | Sunnanväder et al. . | |
| 4,960,412 | 10/1990 | Fink . | |
| 4,978,341 | 12/1990 | Niederhauser . | |
| 5,000,745 | 3/1991 | Guest et al. . | |
| 5,009,391 | 4/1991 | Steigerwald . | |
| 5,009,643 | 4/1991 | Reich et al. . | |
| 5,041,095 | 8/1991 | Littrell . | |
| 5,053,014 | 10/1991 | Van Heugten . | |
| 5,053,016 | 10/1991 | Lander . | |
| 5,104,383 | 4/1992 | Shichman . | |
| 5,104,389 | 4/1992 | Deem et al. . | |
| 5,127,626 | 7/1992 | Hilal et al. . | |
| 5,127,909 | 7/1992 | Shichman . | |
| 5,197,955 | 3/1993 | Stephens et al. | 604/256 |
| 5,211,370 | 5/1993 | Powers | 251/212 |
| 5,211,633 | 5/1993 | Stouder, Jr. | 604/256 |
| 5,221,264 | 6/1993 | Wilk et al. | 604/256 |

STABILIZER FOR A VALVE ASSEMBLY FOR INTRODUCING INSTRUMENTS INTO BODY CAVITIES

BACKGROUND OF THE INVENTION

1. Field of the Invention

The present invention relates to insufflation cannula assemblies adapted to receive an obturator, endoscope or other surgical instrument and more particularly, relates to a stabilizer assembly for providing support to instruments inserted within a cannula assembly while maintaining insufflation during insufflatory surgical procedures.

2. Description of the Related Art

In laparoscopic procedures, surgery is performed in the interior of the abdomen through a small incision; in endoscopic procedures surgery is performed in any hollow viscus of the body through narrow tubes or cannula inserted through a small entrance incision in the skin. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated.

Insufflation involves filling a body cavity with a pressurized gas to maintain the cavity under a certain predetermined pressure. One way of performing the surgery is by first puncturing the skin in a desired body cavity region with a needle. The needle, commonly known as a Verres needle, includes a stylet which introduces an insufflation gas into the body cavity to inflate it.

A trocar assembly, comprised of a cannula assembly and an obturator, is then used to puncture the body cavity. Once the trocar assembly is properly inserted, the obturator may then be removed from the cannula assembly. This frees the lumen therein for the insertion of elongated endoscopes or instruments through the cannula to allow the surgeons to either view the anatomical cavity or perform surgical functions within the cavity, respectively.

Without the obturator to block the flow of insufflation gas out from the cavity, other means must be provided to maintain a relatively fluid-tight interface between the abdominal cavity and the outside atmosphere. Generally, there are two different sealing requirements for trocar cannulas. The first requirement is to provide a substantially fluid-tight seal when an instrument is not being introduced into or is not already present in the cannula. The second requirement is to provide a substantially fluid-tight seal when an instrument is being introduced into or is already present in the cannula.

An additional specification must be met in each of the two situations presented above. During a typical laparoscopic or endoscopic procedure, a single cannula, inserted in an incision, may be required at one point during the procedure to provide access to the surgical site for an instrument having a particular diameter. At other points during the surgery, the same cannula may be required to provide access for numerous other instruments each having a different diameter. This versatility is necessary because there is a limit to the number of cannulas which may be introduced through the skin to provide access to the insufflated cavity.

To meet the first sealing requirement, various types of cannula or trocar assemblies are provided with valves for maintaining a certain gas pressure in the cavity when no trocar or other surgical instrument is present in the cannula. These type of valves are generally effective for maintaining the pneumoperitoneum. For example, one form of cannula assembly incorporates a pivotally mounted flapper valve which is automatically opened upon insertion of an obturator or other instrumentation. Conventional flapper valves may also be manually opened by pivoting a lever provided on the exterior of the housing. An example of such a flapper valve is disclosed in U.S. Pat. No. 4,943,280 to Lander.

For the second sealing requirement, cannula assemblies have been developed which are provided with a series of resilient sealing elements having a central aperture, e.g., commonly assigned, co-pending applications Ser. No. 07/874,291 filed Apr. 24, 1992 and Ser. No. 07/873,416 filed Apr. 24, 1992. Upon insertion, an instrument passes through the sealing element and deforms the aperture so that a seal is maintained around the instrument.

Stretching of the seal element aperture may occur when an instrument is being manipulated by the surgeon. Since the seal elements must be resilient in order to accommodate different diameter instruments, manipulation causing lateral motion of the instrument with respect to the cannula housing will also stretch the apertures of the seal elements, again creating small openings for insufflation gases to escape.

Attempts have been made, by such seal assemblies as noted above, to provide a valve assembly which both accommodates instruments of different diameters and maintains the integrity of the seal between the body cavity and the atmosphere outside the patient's body. However, seal systems developed to date have failed to fully address the insufflation maintenance problem during the period when instruments are being inserted into or are already present in the cannula.

One solution to this problem would be to provide cannulas having more rigid sealing members which are capable of receiving instruments having the same diameter. This solution would not be very practical, however, because it would require far too many cannulas be inserted near the surgical site. For one reason, the cumulative minor gas losses from each cannula would defeat the very purpose of having such specifically designed cannulas. Another reason is that the advantages of minimally invasive surgery would be reduced. That is, the patient would have an increased number of trocar incision wounds which would lengthen the healing process. Additionally, the greater number of cannulas would complicate logistics during surgery, e.g., there would be a greater number of instruments to be monitored, thereby increasing, inter alia, the demands placed on the operating room personnel.

A need therefore exists for a valve assembly which may be incorporated into a cannula assembly or utilized in combination with any type of tubular member for providing access into the body of a patient, while permitting introduction of instruments, differing in diameter from one to the next, through the valve assembly into the body with reduced loss of insufflation gases.

SUMMARY OF THE INVENTION

The present invention provides a novel stabilizer useful for stabilizing surgical instruments inserted through insufflation trocar cannulas having a valve assembly and includes a lightweight and easy to use assembly which may be operated quickly and efficiently. The invention is easy to manufacture and is usable with currently available trocar cannulas.

A stabilizer assembly for use with a valve assembly is provided, wherein the valve assembly accommodates the introduction of surgical instruments into a patient's body through a passageway while maintaining a substantially fluid tight seal, the stabilizer assembly comprises a body portion defining an aperture of a predetermined size in communication with the passageway, and means operatively associated with the body portion, for selectively varying the size of the aperture.

Preferably, the varying means includes at least one movable rigid member slidably disposed within the body portion whereby upon selective movement of the rigid member, the aperture is partially covered by the rigid member thereby reducing the area in which the instrument may move with respect to the stabilizer assembly body portion. In an alternative embodiment the selective varying means includes a pair of rigid members slidably mounted in the body portion in opposed sliding cooperation with respect to each other.

In another alternative embodiment, the invention includes a stabilizer assembly for supporting a surgical instrument inserted in an insufflation trocar cannula having a valve assembly disposed therein, which comprises housing means having an aperture formed therein sufficient to allow passage of surgical instruments therethrough, and rigid instrument support means operatively mounted within the housing means, for selectively applying rigid support to a surgical instrument inserted through the aperture, whereby a surgeon can selectively apply the rigid support means to the instrument such that the instrument is substantially stabilized with respect to a valve assembly of the insufflation trocar cannula assembly.

In one embodiment actuating means operatively associated with the instrument support means are provided, whereby a surgeon can selectively apply the rigid support means to the instrument such that the instrument is substantially stabilized with respect to a valve assembly of the insufflation trocar cannula assembly.

A valve assembly for use with surgical instruments is provided, to maintain a substantially fluid-tight seal during the introduction and presence of surgical instruments in the valve assembly while permitting manipulation of the instruments in a patient's body. The valve assembly comprises a valve body defining a passageway therethrough, means mounted within the valve body, for sealing the passageway both prior to and while an instrument is inserted therein and a stabilizer assembly defining an aperture of a predetermined size which communicates with the passageway. The stabilizer assembly includes aperture varying means for selectively varying the size of the stabilizer assembly aperture.

In an alternative embodiment, the invention provides a cannula assembly for use in a trocar assembly. The cannula assembly is particularly adapted to maintain a substantially fluid-tight seal between the inside of a patient's body and the outside atmosphere. The cannula assembly comprises an elongated sheath having a proximal end and a distal end, a valve housing mounted near the proximal end of the elongated sheath, at least one valve means, positioned within the valve housing, configured and dimensioned to allow passage of a surgical instrument therethrough while providing a substantially fluid-tight seal both prior to insertion of the surgical instrument therein and after the surgical instrument is positioned therein, and a stabilizer assembly defining an aperture of a predetermined size, which is in communication with the passageway, the stabilizer assembly including aperture varying means for selectively varying the size of the stabilizer assembly aperture.

BRIEF DESCRIPTION OF THE DRAWINGS

The foregoing features of the present invention will become more readily apparent and will be understood by referring to the following detailed description of preferred embodiments of the invention, which are described hereinbelow with reference to the drawings wherein.

DETAILED DESCRIPTION OF THE PREFERRED EMBODIMENTS

Figure 1:
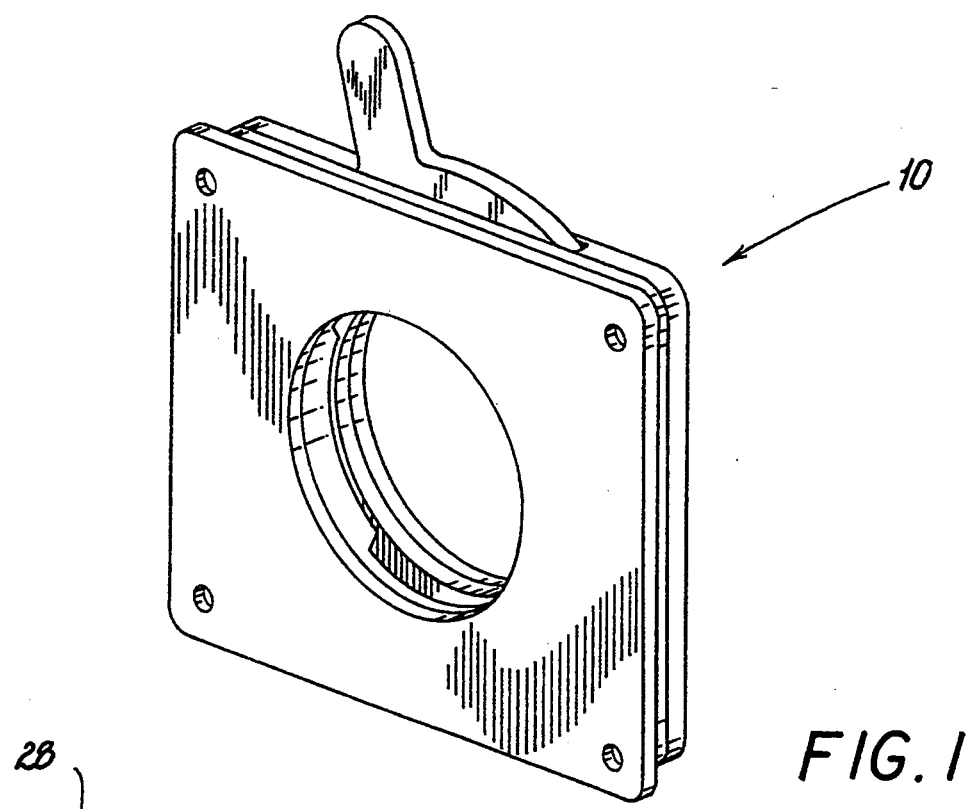
FIG. 1 is a perspective view illustrating one embodiment of the stabilizer assembly of the present invention.

Referring now in specific detail to the drawings, in which like reference numerals identify similar or identical elements throughout the several views, and initially to FIG. 1, which shows one embodiment of the stabilizer assembly of the present invention designated as stabilizer 10. Except where noted otherwise, the materials utilized for the stabilizer assembly include materials such as LEXAN brand polycarbonate available from General Electric Company.

Figure 2A:
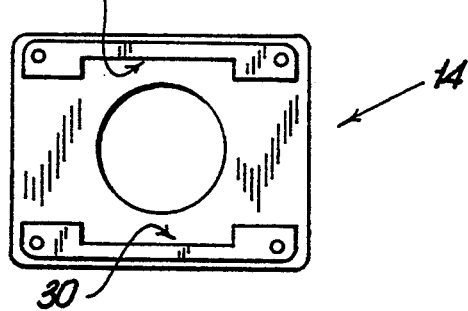
FIG. 2A is a reduced front elevational view of a first body portion of the stabilizer assembly shown in FIG. 2.
Figure 2:
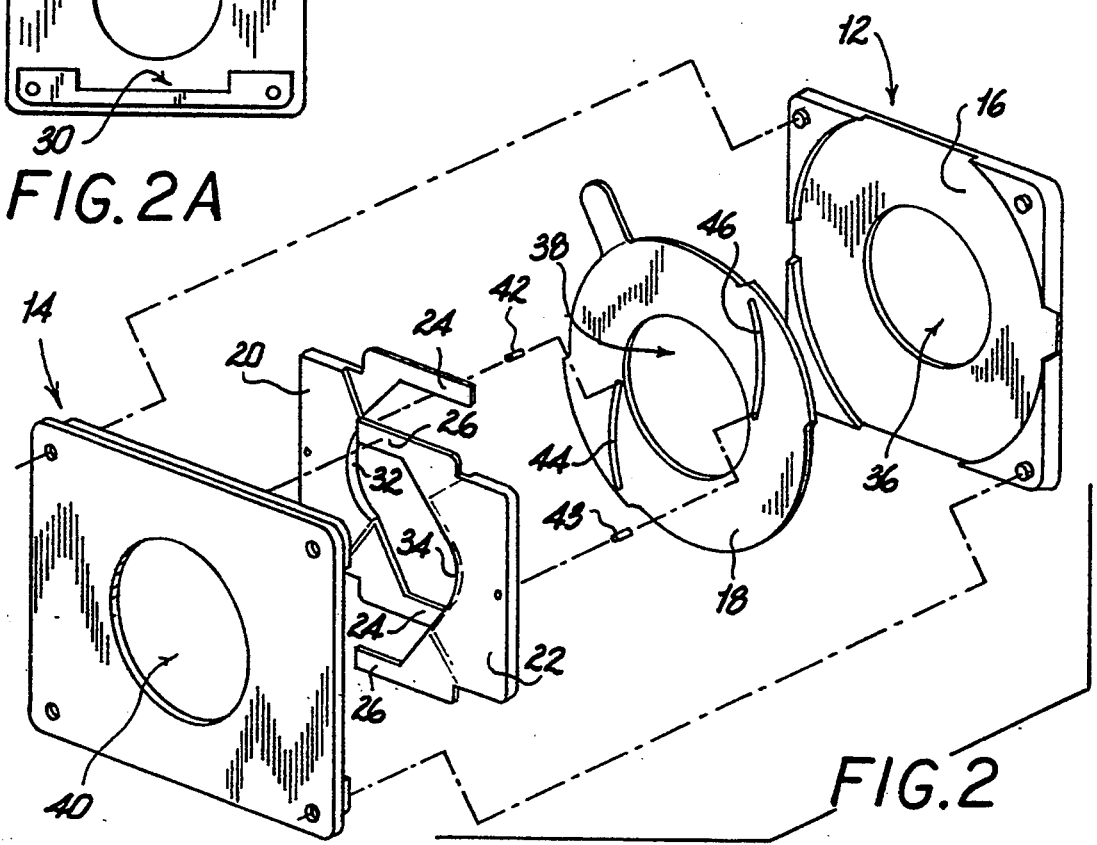
FIG. 2 is an exploded perspective view of the stabilizer assembly shown in FIG. 1.

FIGS. 2 and 2A illustrate the various components making up stabilizer 10. Stabilizer 10 has a housing or body portion formed from cover members 12 and 14 which are attached by any suitable means such as for example friction fitting, welding, adhesives, etc. Cover member 12 has recessed portion 16 formed therein to receive cam 18. In a preferred embodiment, rigid instrument support means, such as a pair of rigid instrument support members are provided, for example, slide plates 20 and 22 which are operatively connected to cam 18. Slide plates 20 and 22 each have aligning means disposed thereon, such as extended portions 24 and 26, respectively, which guide slide plates 20 and 22 in channels 28 and 30, respectively, which are formed on the inside surface of cover member 14.

Slide plates 20 and 22 are preferably U-shaped, i.e. they each have an open side, shown as open ends 32 and 34, respectively, in FIG. 2. The slide plates are mounted within the stabilizer housing formed by covers 12 and 14 such that open ends 32 and 34 are directed toward each other. In this manner, open ends 32 and 34 are substantially aligned with openings 36, 38, and 40, formed in cover member 12, cam 18 and cover member 14, respectively.

Slide plates 20 and 22 are operatively connected to cam 18 by any suitable means, such as, for example, camming pins 42 and 43 being frictionally fitted into bores formed on the inside surface of slide plates 20 and 22, respectively and also fitting in cam slots 44 and 46, respectively, formed on cam 18.

Figure 3:
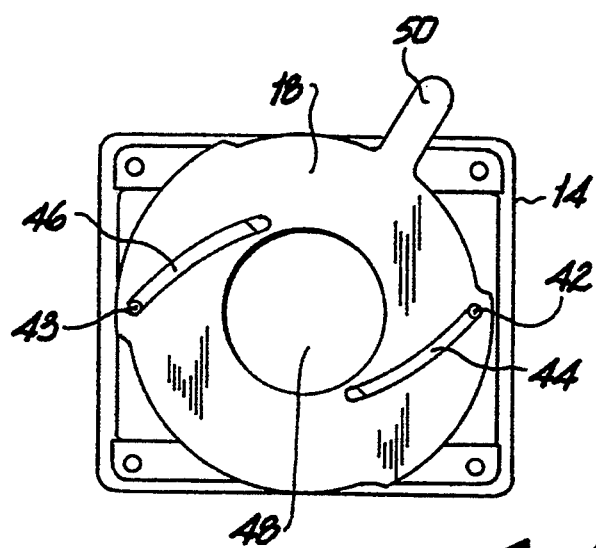
FIGS. 3, 4 and 5 are side elevational views illustrating a partially disassembled stabilizer assembly during a sequence of operations.
Figure 4:
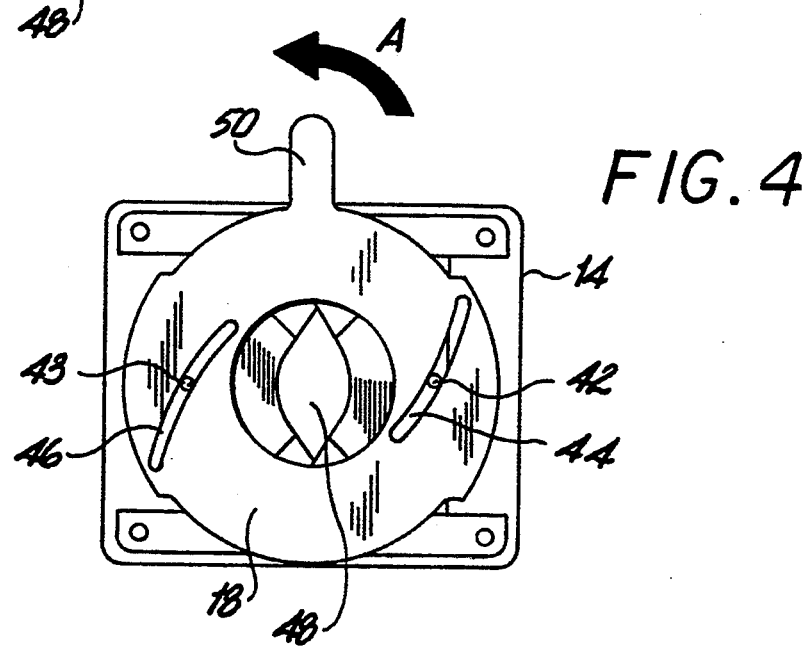
Figure 5:
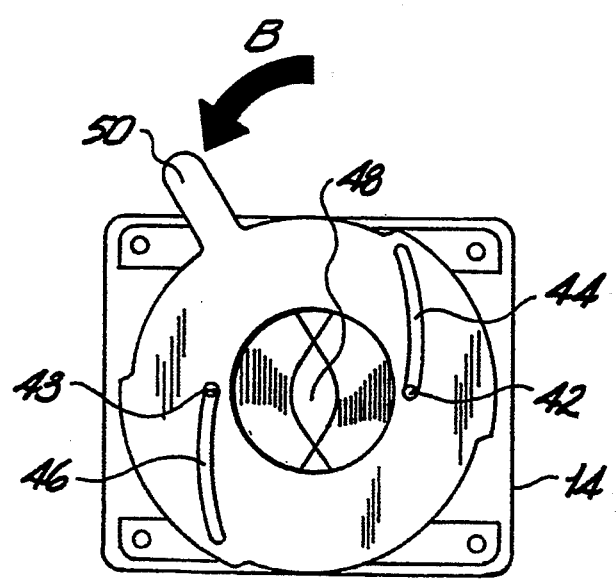

The operation of stabilizer 10 will now be described with reference to FIGS. 3-5, which show stabilizer with cover member 12 removed for illustration purposes. In FIG. 3, cam 18 is shown positioned such that slide plates 20 and 22 are urged to their fully open position. In this orientation, camming pins 42 and 43 are positioned at the outer-most positions of cam slots 44 and 46, respectively, which are adjacent the outer perimeter of cam 18. Aperture 48 is fully opened when cam 18 is situated as shown in FIG. 3.

To reduce the size of aperture 48, a suitable actuation means or control member is actuated to urge slide plates 20 and 22 toward each other. For example, as shown in FIG. 4, when extended portion 50 is rotated in the direction of arrow A, slide plates 20 and 22 are urged toward each other, thereby reducing the size of aperture 48. The full reduction of aperture 48 is completed, as shown in FIG. 5, when extended portion 50 is urged in the direction of arrow B until camming pins 42 and 43 reach the inner-most position of camming slots 44 and 46, respectively. This selective variance of aperture 48 allows stabilizer 10 to provide support to various instruments each having different diameters.

Figure 6:
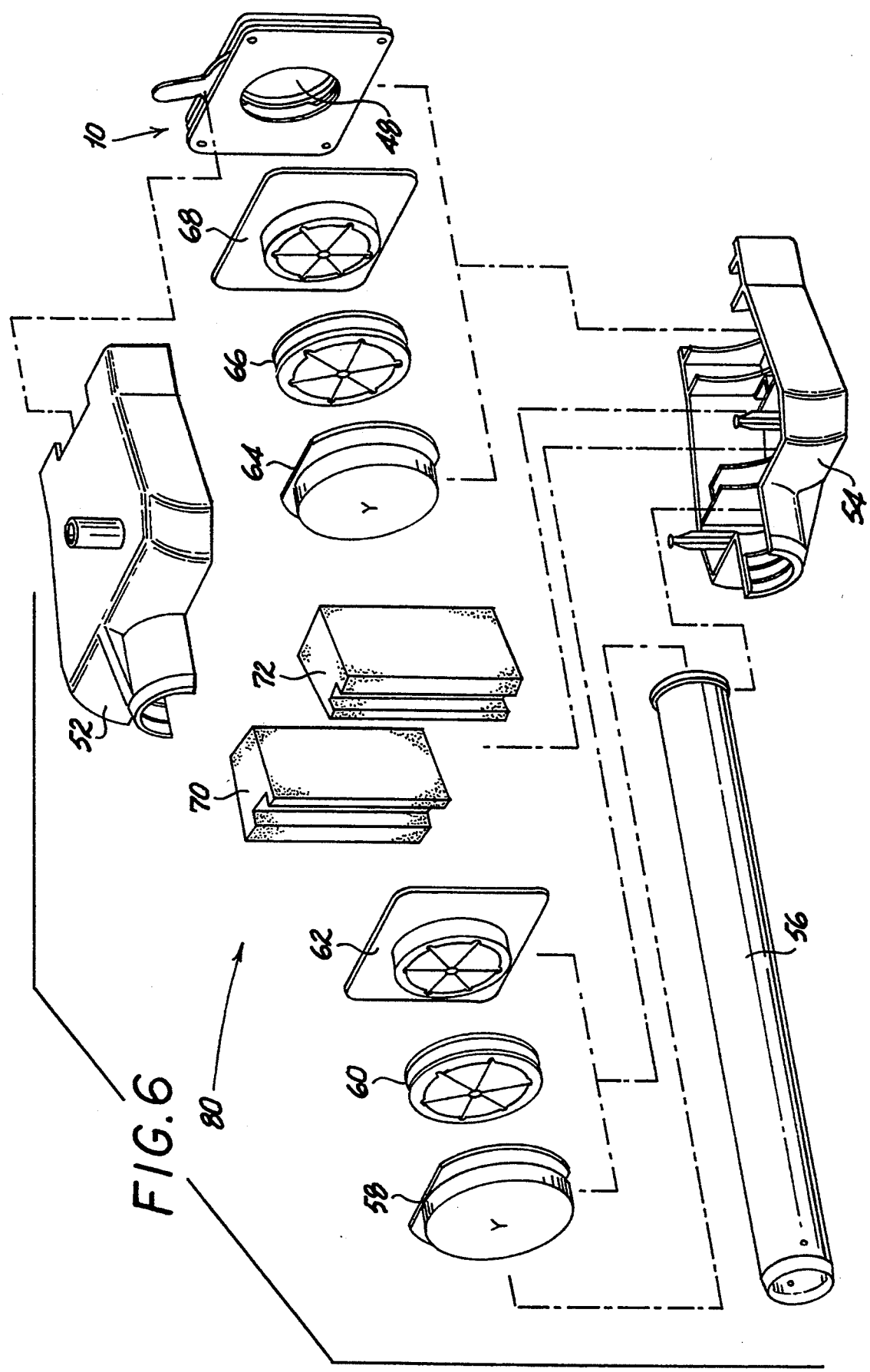
FIG. 6 is an exploded perspective view of one embodiment of a cannula assembly including the stabilizer assembly of the present invention.

FIG. 6 illustrates one embodiment of stabilizer 10 as incorporated in a cannula assembly such as cannula assembly 80. Except where noted otherwise, the materials utilized in the components of the cannula assembly generally include such materials as polycarbonate for housing sections and related components, and stainless steel for such components which transmit forces. One preferred polycarbonate material is LEXAN brand available from General Electric Company. Other specific preferred materials such as nylon or glass filled nylon, for strength, may also be utilized. However, equivalent alternative materials will readily come to the mind of those skilled in the art.

Included in cannula assembly 80 are housing half portions 52 and 54. Cannula sheath 56 is mounted securely between housing half portions 52 and 54. A number of resilient valve components are disposed within housing half portions 52 and 54, which also make-up a valve body or housing. The various seal elements are preferably arranged in series with each other, i.e. a central aperture or slit formed on each seal element is arranged in substantially linear alignment. The seal elements are also preferably arranged in the valve body such that their respective central portions are in alignment with the central longitudinal axis of cannula assembly 80. In FIG. 6, two valve seal element series are shown arranged in the valve body whereby valve elements 58, 60 and 62, are disposed in the lower half of the valve body and valve seal elements 64, 66 and 68 are arranged in the upper portion of valve body. Support means are also provided to give extra support to the housing half portions 52 and 54. For example, support elements 70 and 72 are disposed within housing half portions 52 and 54 and are preferably made of a resilient material such as foam rubber. Stabilizer 10 is mounted at the proximal end of housing half portions 52 and 54 such that aperture 48 is substantially aligned with the linearly aligned apertures of the respective valve seal elements.

Figure 7:
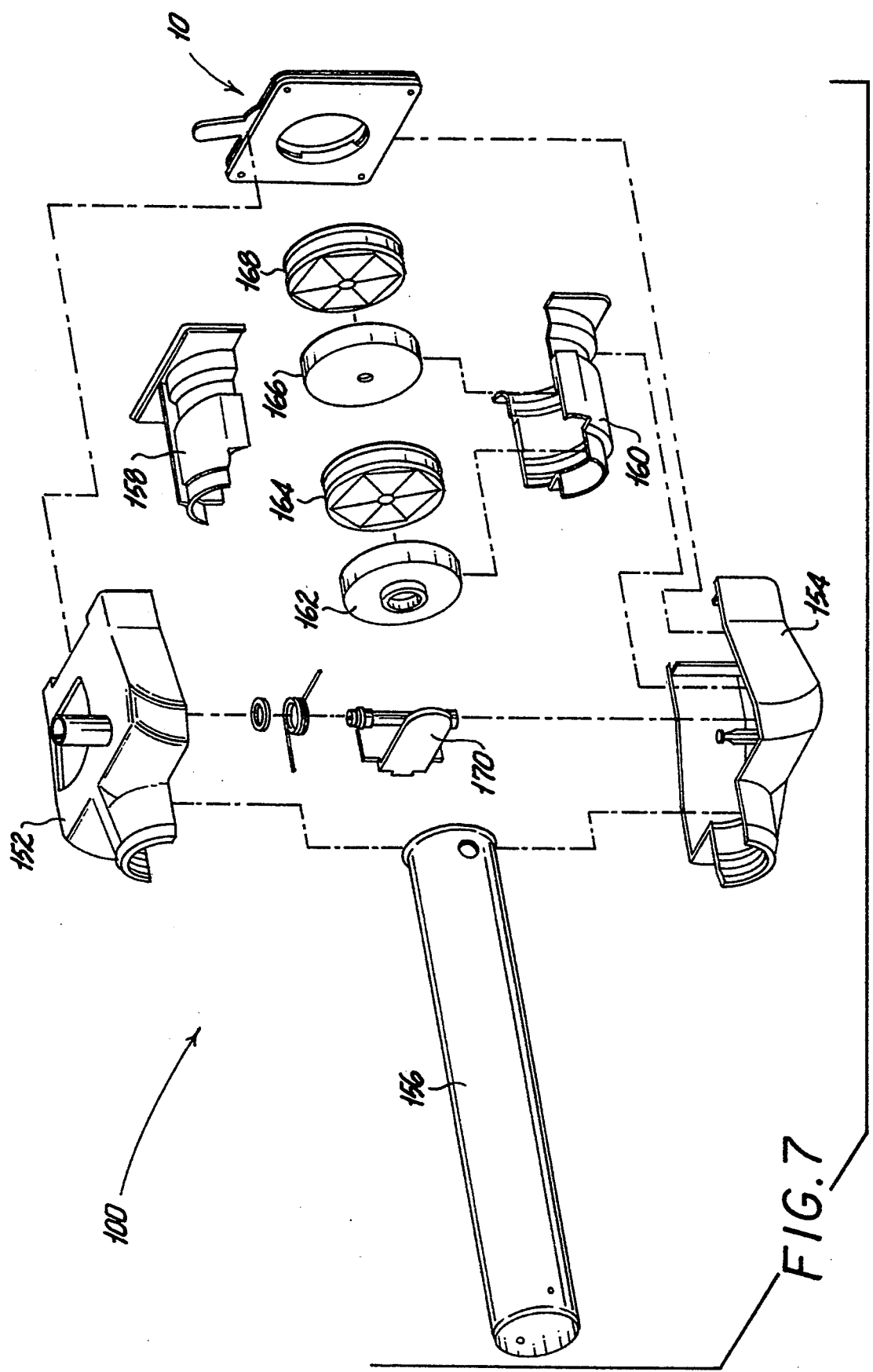
FIG. 7 is an exploded perspective view of another embodiment of a cannula assembly including the stabilizer assembly of the present invention.

FIG. 7 illustrates another embodiment of a cannula assembly designated as cannula assembly 100, which incorporates stabilizer 10. A similar cannula assembly is the subject of U.S. Pat. No. 4,943,280 to Lander, the contents of which are hereby incorporated by reference. Cannula assembly 100, like cannula assembly 80, also has housing half portions such as half portions 152 and 154 and a cannula sheath 156 securely attached to a distal end thereof. Separate valve body means such as valve body housing half portions 158 and 160 are provided to house a number of resilient valve seal elements such as seal elements 162, 164, 166 and 168. Flapper member 170 is mounted within housing half portions 152 and 154 and is spring biased to seal the valve assembly when no instrument is in place in the passageway extending from the proximal end of the housing half portions 152 and 154 to the distal end of cannula sheath 156.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. An insufflation trocar cannula comprising in combination:
   a body having a cannula extending therefrom;
   a valve assembly disposed in said housing; and
   a stabilizer assembly including:
   (a) housing means independent of the valve assembly having an aperture formed therein sufficient to allow passage of surgical instruments therethrough; and
   (b) rigid instrument support means operatively mounted within said housing means and defining an orifice, for selectively applying rigid support to a surgical instrument inserted through said aperture wherein said orifice of said rigid instrument support means are infinitely adjustable over a predetermined range of motion to accommodate different surgical instruments each having a different diameter within said predetermined range;
   whereby a surgeon can selectively apply said rigid support means to said instrument such that said instrument is substantially stabilized with respect to the valve assembly of said insufflation trocar cannula assembly.

2. An insufflation trocar cannula assembly comprising in combination:
   a body having a cannula extending therefrom;
   a valve assembly disposed in said body; and
   a stabilizer assembly associated with said body, said stabilizer assembly including:
   (a) housing means independent of the valve assembly having an aperture formed therein; and
   b) rigid instrument support means defining an orifice and being operatively mounted within said housing means, for selectively applying rigid support to a surgical instrument inserted within an insufflation trocar cannula assembly wherein said orifice of said rigid instrument support means is infinitely adjustable over a predetermined range of motion to accommodate different surgical instruments each having a different diameter within said predetermined range; and
   (c) actuating means operatively associated with said instrument support means whereby a surgeon can selectively apply said rigid support means to said instrument such that said instrument is substantially stabilized with respect to the valve assembly of said insufflation trocar cannula assembly.

3. An insufflation trocar cannula comprising, in combination:
   a housing;
   a valve assembly disposed in said housing; and
   a stabilizer assembly associated with said housing, said stabilizer assembly including:
   (a) a body portion defining an aperture of a predetermined size in communication with said passageway; and
   (b) means operatively associated with said body portion, for selectively varying the size of said aperture in infinite increments up to said predetermined size.

4. An insufflation trocar cannula according to claim 3 wherein said selective varying means includes at least one movable rigid member slidably disposed within said body portion whereby upon selective movement of said rigid member, said aperture is partially covered by said rigid member thereby reducing the area in which said instrument may move with respect to said stabilizer assembly body portion.

5. An insufflation trocar cannula according to claim 3 wherein said selective varying means includes a pair of rigid members slidably mounted in said body portion in opposed sliding cooperation with respect to each other.

6. An insufflation trocar cannula according to claim 5 wherein said selective varying means further includes an actuating member operatively connected to each of said pair of rigid members, such that upon movement of said actuating member in a first direction, said pair of opposed rigid members move towards each other thereby reducing the size of said aperture and upon movement of said actuating member in a second direction, said pair of opposed rigid members move away from each other thereby enlarging the size of said aperture.

7. A valve assembly for use with surgical instruments to maintain a substantially fluid-tight seal during the introduction and presence of surgical instruments in said valve assembly while permitting manipulation of said instruments in a patient's body, which comprises:
   (a) a valve body defining a passageway therethrough;
   (b) means mounted within said valve body, for sealing said passageway both prior to and while an instrument is inserted therein said sealing means defining a first aperture having a predetermined initial size; and
   (c) a stabilizer assembly defining a second aperture of a predetermined size which communicates with said passageway, said stabilizer assembly including aperture varying means for selectively varying the size of said second aperture in a plurality of increments.

8. A valve assembly according to claim 7 wherein said selective aperture varying means includes at least one movable rigid member slidably disposed within said body portion, whereby upon selective movement of said rigid member, said second aperture is partially covered by said rigid member, such that the area in which said instrument may move with respect to said stabilizer assembly is reduced.

9. A valve assembly according to claim 7 wherein said selective aperture varying means includes a pair of rigid members slidably mounted in said body portion in opposed sliding cooperation with respect to each other.

10. A valve assembly according to claim 9 wherein said stabilizing assembly further comprises actuating means operatively connected to each rigid member of said pair of rigid members, for actuating movement of said rigid members, such that upon movement of said actuating means in a first direction, said pair of opposed rigid members move towards each other thereby reducing the size of said second aperture and upon movement of said actuating means in a second direction, said pair of opposed rigid members move away from each other, thereby enlarging the size of said second aperture.

11. A cannula assembly for use in a trocar assembly, said cannula assembly adapted to maintain a substantially fluid-tight seal between the inside of a patient's body and the outside atmosphere, said cannula assembly comprising:
   (a) an elongated sheath having a proximal end and a distal end;
   (b) a valve housing defining a passageway therethrough and mounted near said proximal end of said elongated sheath;
   (c) at least one valve means, positioned within said valve housing, configured and dimensioned to allow passage of a surgical instrument therethrough while providing a substantially fluid-tight seal both prior to insertion of said surgical instrument therein and after said surgical instrument is positioned therein; and
   (d) a stabilizer assembly defining an aperture of a predetermined size, which is in communication with said passageway, said stabilizer assembly including aperture varying means for selectively varying the size of said stabilizer assembly aperture in infinite increments to accommodate different instruments having different diameters.

12. A cannula assembly according to claim 11, wherein said selective aperture varying means includes at least one movable rigid member slidably disposed within said body portion whereby upon selective movement of said rigid member said stabilizer assembly aperture is partially covered by said rigid member thereby reducing the area in which said instrument may move with respect to said stabilizer assembly.

13. A cannula assembly according to claim 11, wherein said selective aperture varying means includes a pair of rigid members slidably mounted in said body portion in opposed sliding cooperation with respect to each other.

14. A cannula assembly according to claim 13, wherein said stabilizer assembly further comprises actuating means operatively connected to each rigid member of said pair of rigid members, for actuating movement of said rigid members, such that upon movement of said actuating means in a first direction, said pair of opposed rigid members move towards each other, thereby reducing the size of said stabilizer assembly aperture and upon movement of said actuating means in a second direction, said pair of opposed rigid members move away from each other enlarging the size of said stabilizer assembly aperture.

* * * * *